United States Patent [19]

Erickson

[11] Patent Number: 4,474,792
[45] Date of Patent: Oct. 2, 1984

[54] N-TETRAZOLYL BENZAMIDES AND ANTI-ALLERGIC USE THEREOF

[75] Inventor: Edward H. Erickson, Woodbury, Minn.

[73] Assignee: Riker Laboratories, Inc., St. Paul, Minn.

[21] Appl. No.: 326,852

[22] Filed: Dec. 3, 1981

Related U.S. Application Data

[63] Continuation-in-part of Ser. No. 49,281, Jun. 18, 1979, abandoned.

[51] Int. Cl.³ .................... A61K 31/41; C07D 257/04
[52] U.S. Cl. .................................... 424/269; 548/253
[58] Field of Search ..................... 548/253; 424/269

[56] References Cited

U.S. PATENT DOCUMENTS

| 3,887,574 | 6/1975 | Ellis et al. | 260/308 D |
| 3,932,416 | 1/1976 | Bays et al. | 260/287 F |
| 4,146,631 | 3/1979 | Ford et al. | 424/269 |
| 4,147,694 | 4/1979 | Erickson | 546/169 |
| 4,232,024 | 11/1980 | Winter et al. | 424/251 |

OTHER PUBLICATIONS

Journal of the Indian Chemical Society 31, 194 (1954).
"Immunology", 16, 749 (1969).

*Primary Examiner*—Paul M. Coughlan, Jr.
*Assistant Examiner*—D. B. Springer
*Attorney, Agent, or Firm*—Donald M. Sell; James A. Smith; Robert W. Sprague

[57] ABSTRACT

Amides obtained by condensing aminotetrazole with optionally substituted ortho-alkoxybenzoic and ortho-methylthiobenzoic acids are potent anti-allergic agents.

18 Claims, No Drawings

N-TETRAZOLYL BENZAMIDES AND ANTI-ALLERGIC USE THEREOF

RELATED APPLICATION DATA

This application is a continuation-in-part of application Ser. No. 049,281, filed June 18, 1979, abandoned.

TECHNICAL FIELD

This invention relates to physiologically active compounds which are amides obtained by condensing aminotetrazole with optionally substituted ortho-alkoxybenzoic or ortho-methylthiobenzoic acids. The invention also relates to anti-allergic compositions containing the compounds and to an anti-allergic method which comprises applying a compound of the invention to a mammalian organism in need thereof.

BACKGROUND ART

Phenol derivatives which may be named 2-hydroxy-N-(tetrazol-5-yl)benzamides are known to exhibit anti-allergic properties (see U.S. Pat. No. 4,146,631). Other less closely related derivatives of aminotetrazole are also known to exhibit anti-allergic properties, e.g., the 8-(1H-tetrazol-5-ylcarbamoyl)quinolines and salts thereof described in U.S. Pat. No. 4,147,694 (and assigned to the assignee of the present invention), the amides of aminotetrazole and quinaldic acid described in U.S. Pat. No. 3,932,416, and the amides of aminotetrazole and acids of chromone, xanthone or anthraquinone described in U.S. Pat. No. 3,887,574.

DISCLOSURE OF INVENTION

The present invention provides, in one aspect, compounds of the formula

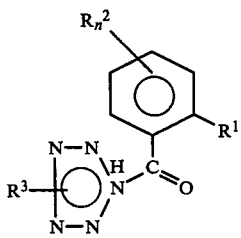

wherein
$R^1$ is methoxy, ethoxy or methylthio;
$R^2$ is halo, lower ($C_{1-4}$) alkyl, lower ($C_{1-4}$) alkoxy, nitro or acetyl;
$R^3$ is hydrogen or methyl; and
n is zero, one or two; provided that when n is two, the $R^2$ groups are selected from halo, methoxy, and alkyl and there is a total of no more than 6 carbon atoms in the $R^2$ groups.

These compounds exhibit unexpectedly good anti-allergic activity, and exceed the anti-allergic activity exhibited by related compounds such as the phenol derivatives of U.S. Pat. No. 4,146,631.

The present invention also provides anti-allergic compositions containing compounds of the invention together with a pharmaceutically acceptable carrier. In addition, the present invention provides a method for inhibiting allergic reactions in mammals which comprises administering compositions of the invention to such mammals.

DETAILED DESCRIPTION

In the foregoing formula, the circle in the tetrazole ring signifies a pair of double bonds which, together with the bonds shown, satisfy all of the valences of the ring carbon atom and all but one valence of the 4 ring nitrogen atoms. The remaining nitrogen valence is satisfied by $R^3$.

In the compounds of the invention in which the tetrazole ring is unsubstituted, the hydrogen atom exists in tautomeric form on either the $N^1$ or the $N^2$ atom, i.e.,

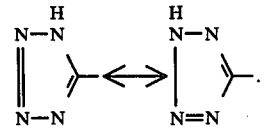

For convenience, however, hydrogen has been depicted herein simply as appearing on the $N^1$ atom. Tautomerism does not occur in the compounds in which the tetrazole ring is substituted with a methyl group, i.e., the substituent methyl group remains in a single location.

Preferred compounds of the invention are those in which $R^1$ is methoxy. If n is one in the compounds of the invention, it is preferred that $R^2$ is 5-halo. Also preferred are compounds of the invention in which any alkyl or alkoxy $R^1$ or $R^2$ groups contain one carbon atom. In addition, it is preferred that $R^3$ is hydrogen.

The preferred compounds of the invention have oral activity and are as follows:
2-methoxy-N-(tetrazol-5-yl)benzamide,
2,3-dimethoxy-N-(tetrazol-5-yl)benzamide,
5-chloro-2-methoxy-N-(tetrazol-5-yl)benzamide,
5-fluoro-2-methoxy-N-(tetrazol-5-yl)benzamide,
5-iodo-2-methoxy-N-(tetrazol-5-yl)benzamide,
5-bromo-2-methoxy-N-(tetrazol-5-yl)benzamide,
3,5-dichloro-2-methoxy-N-(tetrazol-5-yl)benzamide, and
2,4,5-trimethoxy-N-(tetrazol-5-yl)benzamide, and the preparation of these compounds is described below in Example Nos. 1, 4, 12, 13, 14, 15, 18, and 20, respectively.

The compounds of the present invention preferably are prepared by reacting various substituted ortho-alkoxybenzoic acids or ortho-methylthiobenzoic acids (or their respective acid analogs) with 5-aminotetrazole or 5-amino-2-methyl tetrazole. Substituted meta- or para-alkoxybenzoic acids and meta- or para-methylthiobenzoic acids (and their respective acid analogs) do not yield products useful for this invention. The term "benzoic acid" as used in the following paragraphs refers to ortho acids, e.g., 2-methoxybenzoic acid, 2-ethoxybenzoic acid and 2-methylthiobenzoic acid.

Benzoic acid and many substituted benzoic acids or benzoic acid analogs can be prepared by well-established synthetic methods of organic chemistry, e.g., from substituted methoxybenzenes, ethoxybenzenes and methylthiobenzenes. 2-Methoxybenzoic acid and many substituted 2-methoxybenzoic acids can in addition be prepared from substituted salicylic acids.

The preferred method of preparation of the compounds of this invention employs a condensation reaction. Thus, stoichiometrically equivalent amounts of the starting materials (substituted benzoic acids or benzoic acid analogs and 5-aminotetrazole or 5-amino-2-methyltetrazole) are dissolved or suspended in a tertiary organic amine, preferably pyridine. A stoichiometric amount of thionyl chloride is added dropwise to the above mixture (if a hydrated form of aminotetrazole starting material is used, then sufficient additional thionyl chloride is added to react with all the water of hydration). During the thionyl chloride addition, the mixture is preferably maintained at a temperature of between 40° to 90° C. Other temperatures can be used, depending upon the choice of solvent, and the reflux temperature of the mixture is frequently a convenient temperature.

Alternative methods, involving reactions generally known for the synthesis of amides, can also be used to prepare the compounds of the invention. These methods involve carboxy activation, for example via acid chloride, reaction of the carboxylic acid group with N,N'-carbonyl diimidazole, reaction with N,N'-dicyclohexyl carbodiimide to provide an activated adduct, reaction with ethyl chloroformate, n-butyl chloroformate and the like to provide a mixed anhydride, reaction with p-nitrophenoxybenzyl chloride to provide p-nitrophenoxybenzyl ester, and the like. These methods are generally more complex and expensive, and are only used when the preferred method is unsatisfactory.

If it is desired to prepare a (2-methyltetrazol-5-yl)benzamide, the synthetic route preferably involves reaction of a substituted benzoic acid or benzoic acid analog along with 5-amino-2-methyltetrazole, or alternatively can proceed via reaction of a substituted benzoic acid or benzoic acid analog with 5-aminotetrazole followed by methylation of the tetrazole ring. Suitable methylating agents for the latter route are methyl bromide and methyl iodide. Methylation will generally result in a mixture of $N^1$ and $N^2$ substituted compounds. Separation can be carried out by crystallization or chromatography.

Certain substituted 2-methoxybenzoic acid starting materials can be prepared from substituted salicylic acids which are methylated followed by ester hydrolysis. Three methylation techniques can be used to make such starting materials. In the first method, the methylation step is carried out by reaction of salicylic acid with methyl iodide in the presence of silver oxide ($Ag_2O$) in a highly polar organic solvent (preferably N,N-dimethylformamide) at moderate temperature (from about 0° to 100° C.). The second method involves reaction of salicylic acid with methyl iodide in the presence of a weak inorganic base such as potassium carbonate in a highly polar organic solvent (preferably N,N-dimethylformamide) at moderate temperatures (from about 0° to 100° C.). The third method involves reaction of salicylic acid with methyl benzenesulfonate in the presence of sodium hydride in a highly polar organic solvent (preferably N,N-dimethylformamide) at higher temperatures (from about 100° C. to the reflux temperature of the solution). Following methylation by any of these techniques the ortho-methoxybenzoic acid ester is isolated (by standard methods, e.g., precipitation and filtration) then hydrolyzed by heating in a lower alkanol such as ethanol in the presence of a base such as sodium hydroxide. The desired product can be isolated by acidification and filtration.

Certain 4-alkoxy-substituted 2-methoxybenzoic acids (from which compounds of the invention were subsequently prepared) were prepared from substituted methoxybenzene, using a procedure described in the Journal of the Indian Chemical Society 31, 194 (1954). The reaction method proceeds substantially as follows:

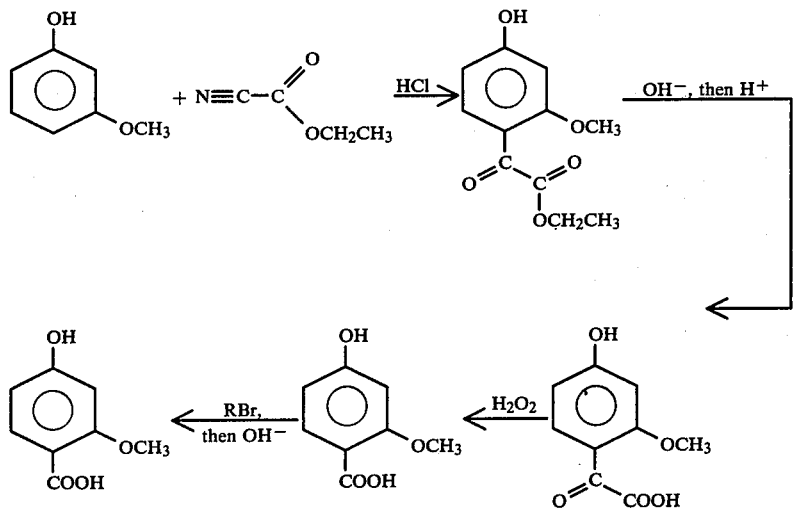

wherein R is preferably lower alkyl ($C_{1-4}$).

The compounds of the invention have been shown to inhibit the release and/or synthesis and/or effect of biochemical products resulting from the combination of certain types of antibody and specific antigen. Both subjective and objective changes which result from the inhalation of specific antigen by sensitized subjects may be markedly inhibited by administration of the new compounds. The new compounds are useful in the treatment of so-called "intrinsic" asthma (in which no sensitivity to extrinsic antigen can be demonstrated) or any other condition in which non-specific factors trigger the release of allergic mediators; as well as in the treatment of other conditions in which specific antigen-antibody reactions are responsible for disease, for example extrinsic asthma, food allergies, allergic rhinitis, allergic conjunctivitis, atopic dermititis, hay fever, urticaria and auto-immune diseases.

The compositions of the invention normally contain a compound of the invention (as active ingredient) in association with a pharmaceutically acceptable carrier or diluent. The nature of the composition and the carrier or diluent will depend upon the desired mode of administration, which may be, for example, orally, by inhalation (orally or nasally), parenterally (as by intradermal or intravenous injection) or by topical application. The compositions can be formulated in the conventional manner with conventional ingredients, e.g., they can be put up as solutions, suspensions, syrups, dry powders, tablets or, when intended for topical application, as creams, lotions or pastes. The compositions of the invention generally contain a minor proportion of the active ingredient and a major proportion of carrier or diluent.

For administration by inhalation the compounds of the invention (optionally in the form of a salt such as the sodium salt) are dissolved or suspended in water and can be applied by means of a conventional nebulizer. However, the administration of medicaments by means of a pressurized dispensing container, i.e., an aerosol dispenser, is an alternative to nebulizer administration. Aqueous solutions for administration by means of a conventional nebulizer can contain up to about 10 percent by weight of the active ingredient in sterile water; and compositions for dispensing from a pressurized container containing suspensions or solutions of active ingredient in liquified propellants normally contain about 0.2 to 5 pecent by weight of the active ingredient.

For administration from an aerosol dispenser the active ingredient is dissolved or suspended in a liquified propellant medium. Suitable propellants are those conveniently used in formulations for dispensing from pressurized containers, for example, of the halogenated hydrocarbon type such as fluorohydrocarbons or fluorohalohydrocarbons and mixtures of any of these together with other propellants (see U.S. Pat. No. 2,686,691). Preferred propellants of low toxicity are difluorodichloromethane, dichlorotetrafluoroethane, and mixtures thereof. Where the active ingredient is not soluble in the propellant, it may be necessary to add a surface-active agent to the composition in order to suspend the active ingredient in the propellant medium. The use of such surface-active agents and the advantages which stem therefrom are more fully described in British Patent Specification No. 1,063,512.

When put up as powders, the compositions of the invention can be administered by means of a conventional insufflator device. In order to improve the properties of the powder for this purpose it is useful to modify the surface characteristics of the powder particles, for example, by coating them with a pharmaceutically acceptable material such as sodium stearate. In addition, finely divided powders containing the active ingredient can be mixed with a coarser diluent material, such as lactose, which can be present in a smaller, equal or greater amount than the amount of active ingredient, for example in from 50 to 150 percent by weight based on the weight of the active ingredient of the invention and such other pharmaceutically active ingredients as may be present.

The compounds of the invention can also be administered by dispensers from which metered amounts of the compound are discharged to be orally or nasally received by inhalation, wherein the propellant is compressed air or any other compressed inert gas such as nitrogen, argon and the like.

As noted previously, the compounds of the invention are indicated for use in inhibiting the effects of antibody-antigen reactions. The treatment regimen may require repeated dosages of the compound at regular intervals. The amount of compound and frequency of administration will depend upon many factors, and no concise dosage rate or regimen can be generally stated. However, as a general guide, where the compounds are administered by inhalation to a patient suffering from acute allergic asthma, therapeutically useful results may be achieved when doses of 0.1 to 20 mg/kg are used. When the compounds are administered by oral routes, larger dosages are normally given. The invention thus provides a method for inhibiting the effects of antibody-antigen reactions by applying to the known or expected site of the antibody reaction a therapeutically effective amount of a compound of the invention.

The compounds of the invention can also be used in the treatment of allergic eye conditions, for example, those associated with hay fever, i.e., allergic conjunctivitis. For such use the compounds of the invention can be used in the form of eye drops and/or spray as an isotonic aqueous solution containing about two percent of the compound and a preservative.

Other active ingredients can also be present in the compositions of the invention. Thus, in compositions for administration by inhalation, it can be beneficial to include a bronchodilator such as isoprenaline, adrenaline, carbuterol, rimiterol, orciprenaline, isoetharine, or derivatives thereof, particularly salts. The amount of bronchodilator used will vary over a broad range, depending, inter alia, upon the nature and activity of the bronchodilator and the compound of the present invention which is used. However, the use of a minor proportion (i.e., less than 50 percent by weight) of the bronchodilator together with from 0.1 to 10 percent by weight of a compound of the present invention is preferred. Such compositions constitute an additional aspect of the invention.

The effectiveness of the compounds of the invention is evaluated by inhibiting passive cutaneous anaphylaxis in a standard test method substantially as described in "Immunology", 16, 749 (1969). The variation of the method generally used is as follows: Sprague-Dawley rats (male or female) having a body weight of about 200 grams are injected intramuscularly with egg albumin and intraperitoneally with *Bordetella pertussis* vaccine. Ten to twelve days after this treatment the rats are exsanguinated via the abdominal aorta to recover the blood, which is allowed to clot overnight. The blood samples are centrifuged in order to remove the blood serum containing the antibody.

This antibody is used in the following way: Sprague-Dawley rats weighing from 50 to 120 grams are sensitized by intradermal injection of 0.1 ml. of antibody-containing serum into the mid-dorsal region. Sensitivity is allowed to develop for 24 hours, and the test compounds are administered (either by intraperitoneal injection or orally) at dose levels selected to provide a range of inhibition values (suitable screening doses are 50, 25, 10 or 5 mg/kg). Six rats are used for each concentration of the compound under test. At various times thereafter (e.g., five minutes), the rats are then injected intravenously with an antigen which contains 1 ml. of a mixture of egg albumin (0.5 mg/ml), Evans Blue dye solution (10 mg/ml) and physiological saline solution. Six rats are also used as controls for each test, the control rats being injected with the antibody and the antigen in the same way as the test rats but receiving no test compounds. Forty-five minutes after injection of the egg albumin the rats are killed and the skins removed and reversed. The intensity of the anaphylactic reaction is assessed by measuring the area of the characteristic blue weal produced by spread of the Evans Blue dye from the sensitization site, with this area being determined approximately by taking the product of two diameters of the dyed area at right angles to one another. The greater the anaphylactic reaction, the larger is the area of the blue weal. Percent inhibitions are calculated using the formula $$\frac{(\text{Control Group Area} - \text{Treated Group Area}) \times 100}{\text{Control Group Area}}$$

and these values are plotted graphically for each compound so that the dosage required to achieve a 50 percent inhibition of the anaphylactic reaction can be determined. The compounds of the invention are active in this test at non-toxic doses, and exhibit percent inhibition of 30 percent or greater at a 5 mg. dose. The preferred compounds of the invention of Example Nos. 1, 4, 12, 13, 14, 15, 18, and 20 exhibit 94, 79, 89, 85, 100, 86, 88, and 79 percent inhibition, respectively, in the above test at a 5 mg dose.

The following examples are provided for the purpose of further illustrating the invention but are not intended to limit the scope thereof in any way.

EXAMPLE 1

To a solution of 0.1 mole of 2-methoxybenzoic acid and 0.12 mole of 5-aminotetrazole monohydrate in 200 ml. of pyridine was added 16 ml. of thionyl chloride. After stirring for about one hour at 40° to 60° C. the solution was evaporated under vacuum. The residue was diluted with aqueous sodium hydroxide and filtered. The solution was acidified with hydrochloric acid and the resulting solid product separated therefrom by filtration, drying and recrystallization from ethanol. The white solid product was 2-methoxy-N-(tetrazol-5-yl)benzamide, m.p. 242°-243° C.

| Analysis: | % C | % H | % N |
|---|---|---|---|
| Calculated for $C_9H_9N_5O_2$: | 49.3 | 4.1 | 32.0 |
| Found: | 49.0 | 4.1 | 32.2 |

Using the method of Example 1, the following compounds of the invention were prepared from the starting benzoic acid-type intermediates listed below in Table I.

TABLE I

| Ex. no. | Starting material | Product (m.p. °C.) |
|---|---|---|
| 2 | 2-ethoxybenzoic acid | 2-ethoxy-N-(tetrazol-5-yl)benzamide, m.p. 257-258 |
| 3 | 3-methyl-2-methoxybenzoic acid | 3-methyl-2-methoxy-N-(tetrazol-5-yl)benzamide, m.p. 258-263 |
| 4 | 2,3-dimethoxybenzoic acid | 2,3-dimethoxy-N-(tetrazol-5-yl)benzamide, m.p. 234-235 |
| 5 | 2,4-dimethoxybenzoic acid | 2,4-dimethoxy-N-(tetrazol-5-yl)benzamide, m.p. 252-264 |

TABLE I-continued

| Ex. no. | Starting material | Product (m.p. °C.) |
|---|---|---|
| 6 | 4-nitro-2-methoxybenzoic acid (O₂N, OCH₃, COOH) | corresponding tetrazolyl amide; m.p. 275–278 |
| 7 | 4-n-butoxy-2-methoxybenzoic acid (n-C₄H₉O, OCH₃, COOH) | corresponding tetrazolyl amide; m.p. 232–234 |
| 8 | 4-chloro-2-methoxybenzoic acid (Cl, OCH₃, COOH) | corresponding tetrazolyl amide; m.p. 255–257 |
| 9 | 2,5-dimethoxybenzoic acid (OCH₃, CH₃O, COOH) | corresponding tetrazolyl amide; m.p. 255–258 |
| 10 | 2-methoxy-5-methylbenzoic acid (OCH₃, CH₃, COOH) | corresponding tetrazolyl amide; m.p. 249–253 (dec.) |
| 11 | 2-methoxy-5-nitrobenzoic acid (OCH₃, O₂N, COOH) | corresponding tetrazolyl amide; m.p. 257–258 |
| 12 | 5-chloro-2-methoxybenzoic acid (OCH₃, Cl, COOH) | corresponding tetrazolyl amide; m.p. 250–255 |

TABLE I-continued

| Ex. no. | Starting material | Product (m.p. °C.) |
|---|---|---|
| 13 | 2-methoxy-5-fluoro-benzoic acid | 2-methoxy-5-fluoro-N-(1H-tetrazol-5-yl)benzamide<br>m.p. 248–255 |
| 14 | 2-methoxy-5-iodo-benzoic acid | 2-methoxy-5-iodo-N-(1H-tetrazol-5-yl)benzamide<br>m.p. 255–259 (dec.) |
| 15 | 5-bromo-2-methoxy-benzoic acid | 5-bromo-2-methoxy-N-(1H-tetrazol-5-yl)benzamide<br>m.p. 258–260 (dec.) |
| 16 | 5-acetyl-2-methoxy-benzoic acid | 5-acetyl-2-methoxy-N-(1H-tetrazol-5-yl)benzamide<br>m.p. 264–266 |
| 17 | 2,6-dimethoxy-benzoic acid | 2,6-dimethoxy-N-(1H-tetrazol-5-yl)benzamide<br>m.p. 275–280 |
| 18 | 3,5-dichloro-2-methoxy-benzoic acid | 3,5-dichloro-2-methoxy-N-(1H-tetrazol-5-yl)benzamide<br>m.p. 256–258 |
| 19 | 3,5-diisopropyl-2-methoxy-benzoic acid | 3,5-diisopropyl-2-methoxy-N-(1H-tetrazol-5-yl)benzamide<br>m.p. 205–207 |

TABLE I-continued

| Ex. no. | Starting material | Product (m.p. °C.) |
|---|---|---|
| 20 | 1,2-dimethoxy-4,5-dimethoxy benzoic acid (CH₃O, OCH₃, CH₃O, COOH) | corresponding CNH-tetrazole amide (CH₃O, OCH₃, CH₃O) m.p. 266–269 |
| 21 | 2-(methylthio)benzoic acid (SCH₃, COOH) | corresponding CNH-tetrazole amide m.p. 272–274 |

In order to more clearly illustrate the synthetic methods of the invention, the methods used to prepare the benzoic acid-type starting materials shown in Table I are further described below.

EXAMPLE 22

Step A

A mixture of 3-methoxyphenol (22 g.) and ethyl cyanoformate (25 g.) in 200 ml. of diethyl ether was saturated with dry hydrogen chloride at 5° C. After standing two days at 5° C. and one day at 25° C., the heavy red layer was collected and cautiously mixed with water. The resulting mixture was extracted wth diethyl ether. The ether layer was evaporated and the residue recrystallized from water to provide the desired intermediate ethyl 4-hydroxy-2-methoxybenzoxalate (m.p. 131°–135° C. after further recrystallization from benzene, literature m.p. 135°–136° C.).

Step B

The intermediate of Step A was heated at reflux in 5 percent sodium hydroxide solution for 20 minutes on a steam bath. Acidification provided the solid free acid. This solid acid was heated at reflux in 10 percent hydrogen peroxide solution for about one hour. On cooling, the desired 4-hydroxy-2-methoxybenzoic acid was obtained as a solid precipitate.

Step C

A mixture of 4.2 g. (0.025 mole) of 4-hydroxy-2-methoxybenzoic acid, 7 g. of potassium carbonate, and 10 g. of n-butyl bromide in 100 ml. of N,N-dimethylformamide was heated at 70° C. for 24 hours. The mixture was cooled, diluted with water and extracted with diethyl ether. The ether extracts were washed with dilute sodium hydroxide solution, then washed with water and dried. The ether was evaporated and the residue heated at reflux for 4 hours in an equivolume mixture of 10 percent sodium hydroxide solution and ethanol. Evaporation followed by acidification provided the desired 4-(n-butoxy)-2-methoxy-benzoic acid (m.p. 94°–96° C. after recrystallizaiton from cyclohexane).

EXAMPLE 23

A mixture of 7.1 g. (0.05 mole) of 3-methylsalicylic acid, 23.1 g. (0.1 mole) of silver oxide and 25 ml. of methyl iodide in 150 ml. of N,N-dimethylformamide was stirred at 25° C. for 16 hours, then filtered. The filtrate was evaporated to provide a residue which was hydrolyzed by heating at 50° C. in an equivolume mixture of ethanol and 6N sodium hydroxide solution. The resulting mixture was acidified and filtered. The filtrate was evaporated, and the residue dissolved in base and treated with decolorizing charcoal. Acidification provided white solid 2-methoxy-3-methylbenzoic acid, m.p. 70°–75° C.

EXAMPLE 25

A mixture of 17.2 g (0.1 mole) of 5-chlorosalicylic acid, 28 g. of potassium carbonate, 25 ml. of methyl iodide, and 100 ml. of N,N-dimethylformamide was heated at 60° C. for 16 hours. The mixture was diluted with water and extracted with diethyl ether. The ether extracts were evaporated and the residue dissolved in benzene. The resulting solution was washed with 5 percent sodium hydroxide solution and dried over magnesium sulfate. Evaporation provided a residue which was mixed with 100 ml. of ethanol and 100 ml. of 10 percent sodium hydroxide solution and heated at reflux for two hours. The mixture was evaporated to provide a residue which was washed with 5 percent hydrochloric acid solution, and recrystallized from carbon tetrachloride to provide white solid 5-chloro-2-methoxybenzoic acid, m.p. 95°98° C.

EXAMPLE 25

A mixture of 7.05 g. (0.042 mole) of 5-methoxysalicyclic acid, 34.4 g. (0.2 mole) of methyl benzenesulfonate, 4.8 g. (0.2 mole) of sodium hydride and 100 ml. of N,N-dimethylformamide was heated at 125° C. for 16 hours, then poured into water. The mixture was extracted with diethyl ether and the extracts washed thrice with 200 ml. portions of 5N sodium hydroxide solution. The extracts were dried over magnesium sulfate, then evaporated to provide a residue which was dissolved in 100 ml. of ethanol and 100 ml. of 1N sodium hydroxide solution. The resulting solution was heated at reflux for 3 hours, then acidified with hydrochloric acid. The resulting solution was extracted with 200 ml. of diethyl ether. The extracts were washed with water, then dried.

Evaporation provided 2,5-dimethoxybenzoic acid, m.p. 80°–85° C.

Using the method of the above Examples, other intermediates used to make compounds of the invention were prepared. Shown below in Table II are the Example no., starting material, intermediate product, and the method (i.e., that of Example No. 24 or 25) by which such intermediate product was prepared.

40 ml. of pyridine was added dropwise 1.0 g (0.008 mole) of thionyl chloride. The mixture was stirred for one hour at 50° C. The stirred mixture was poured into water, acidified, and cooled. The resulting precipitate was collected by filtration and recrystallized from ethanol to provide 1.2 g 2-hydroxy-N-(tetrazol-5-yl)benzamide, in the form of a white solid, m.p. 264°–266° C.

TABLE II

| Ex. No. | Starting material | Intermediate product | Method of Ex. |
|---|---|---|---|
| 26 | 4-methylsalicylic acid (4-CH₃, 2-OH, 1-COOH benzene) | 4-methyl-2-methoxybenzoic acid (4-CH₃, 2-OCH₃, 1-COOH benzene) | 24 |
| 27 | 5-nitrosalicylic acid (5-O₂N, 2-OH, 1-COOH benzene) | 5-nitro-2-methoxybenzoic acid (5-O₂N, 2-OCH₃, 1-COOH benzene) | 24 |
| 28 | 4-methoxy-5-chlorosalicylic acid (4-H₃CO, 5-Cl, 2-OH, 1-COOH benzene) | 2,4-dimethoxy-5-chlorobenzoic acid (4-H₃CO, 5-Cl, 2-OCH₃, 1-COOH benzene) | 24 |
| 29 | 5-fluorosalicylic acid (5-F, 2-OH, 1-COOH benzene) | 5-fluoro-2-methoxybenzoic acid (5-F, 2-OCH₃, 1-COOH benzene) | 24 |
| 30 | 5-iodosalicylic acid (5-I, 2-OH, 1-COOH benzene) | 5-iodo-2-methoxybenzoic acid (5-I, 2-OCH₃, 1-COOH benzene) | 24 |
| 31 | 5-bromosalicylic acid (5-Br, 2-OH, 1-COOH benzene) | 5-bromo-2-methoxybenzoic acid (5-Br, 2-OCH₃, 1-COOH benzene) | 24 |
| 32 | 5-acetylsalicylic acid (5-CH₃CO, 2-OH, 1-COOH benzene) | 5-acetyl-2-methoxybenzoic acid (5-CH₃CO, 2-OCH₃, 1-COOH benzene) | 24 |
| 33 | 3,5-dichlorosalicylic acid (3-Cl, 5-Cl, 2-OH, 1-COOH benzene) | 3,5-dichloro-2-methoxybenzoic acid (3-Cl, 5-Cl, 2-OCH₃, 1-COOH benzene) | 24 |
| 34 | 3,5-diisopropylsalicylic acid (3-(CH₃)₂CH, 5-(CH₃)₂CH, 2-OH, 1-COOH benzene) | 3-isopropyl-5-fluoro-2-methoxybenzoic acid (3-(CH₃)₂CH, 5-F, 2-OCH₃, 1-COOH benzene) | 25 |

In order to compare the anti-allergic activity of compounds of the invention to the anti-allergic activity of the compounds of U.S. Pat. No. 4,146,631, the compound 2-hydroxy-N-(tetrazol-5-yl)benzamide was synthesized and tested as shown below.

COMPARATIVE EXAMPLE

To a solution of 1.4 g (0.01 mole) of salicylic acid and 1.03 g (0.01 mole) of 5-aminotetrazole monohydrate in

| Analysis: | % C | % H | % N |
|---|---|---|---|
| Calculated for C₈H₇N₅O₂: | 46.8 | 3.4 | 34.1 |
| Found: | 46.6 | 3.3 | 34.3 |

When this compound was tested according to the above-described passive cutaneous anaphylaxis inhibition test, it exhibited 61 percent inhibition at a 5 mg. dose. By comparison, the structurally related compound 2-methoxy-N-(tetrazol-5-yl)benzamide (a compound of the present invention) exhibited 94 percent inhibition at the same dose. The compound of the invention therefore indicated significantly higher anti-allergic activity than a corresponding compound of U.S. Pat. No. 4,146,631.

Various modifications and alterations of this invention will be apparent to those skilled in the art without departing from the scope and spirit of this invention and the latter should not be restricted to that set forth herein for illustrative purposes.

What is claimed is:

1. A compound selected from the group consisting of 2-methoxy-N-(tetrazol-5-yl)benzamide, 2,3-dimethoxy-N-(tetrazol-5-yl)benzamide, 5-chloro-2-methoxy-N-(tetrazol-5-yl)benzamide, 5-fluoro-2-methoxy-N-(tetrazol-5-yl)benzamide, 5-iodo-2-methoxy-N-(tetrazol-5-yl)benzamide, 5-bromo-2-methoxy-N-(tetrazol-5-yl)benzamide, 3,5-dichloro-2-methoxy-N-(tetrazol-5-yl)benzamide, and 2,4,5-trimethoxy-N-(tetrazol-5-yl)benzamide.

2. The compound 2-methoxy-N-(tetrazol-5-yl)benzamide according to claim 1.

3. The compound 2,3-dimethoxy-N-(tetrazol-5-yl)benzamide according to claim 1.

4. The compound 5-chloro-2-methoxy-N-(tetrazol-5-yl)benzamide according to claim 1.

5. The compound 5-fluoro-2-methoxy-N-(tetrazol-5-yl)benzamide according to claim 1.

6. The compound 5-iodo-2-methoxy-N-(tetrazol-5-yl)benzamide according to claim 1.

7. The compound 5-bromo-2-methoxy-N-(tetrazol-5-yl)benzamide according to claim 1.

8. The compound 3,5-dichloro-2-methoxy-N-(tetrazol-5-yl)benzamide according to claim 1.

9. The compound 2,4,5-trimethoxy-N-(tetrazol-5-yl)benzamide according to claim 1.

10. A method for inhibiting the result of antibody-antigen reaction in a mammal which comprises administering to said mammal a therapeutically effective amount of an anti-allergic composition comprising a therapeutically effective amount of an anti-allergic compound and a pharmaceutically acceptable carrier, said anti-allergic compound being selected from the group consisting of 2-methoxy-N-(tetrazol-5-yl)benzamide, 2,3-dimethoxy-N-(tetrazol-5-yl)benzamide, 5-chloro-2-methoxy-N-(tetrazol-5-yl)benzamide, 5-fluoro-2-methoxy-N-(tetrazol-5-yl)benzamide, 5-iodo-2-methoxy-N-(tetrazol-5-yl)benzamide, 5-bromo-2-methoxy-N-(tetrazol-5-yl)benzamide, 3,5-dichloro-2-methoxy-N-(tetrazol-5-yl)benzamide and 2,4,5-trimethoxy-N-(tetrazol-5-yl)benzamide.

11. A method according to claim 10, wherein said composition comprises 2-methoxy-N-(tetrazol-5-yl)benzamide.

12. A method according to claim 10, wherein said composition comprises 2,3-dimethoxy-N-(tetrazol-5-yl)benzamide.

13. A method according to claim 10, wherein said composition comprises 5-chloro-2-methoxy-N-(tetrazol-5-yl)benzamide.

14. A method according to claim 10, wherein said composition comprises 5-fluoro-2-methoxy-N-(tetrazol-5-yl)benzamide.

15. A method according to claim 10, wherein said composition comprises 5-iodo-2-methoxy-N-(tetrazol-5-yl)benzamide.

16. A method according to claim 10, wherein said composition comprises 5-bromo-2-methoxy-N-(tetrazol-5-yl)benzamide.

17. A method according to claim 10, wherein said composition comprises 3,5-dichloro-2-methoxy-N-(tetrazol-5-yl)benzamide.

18. A method according to claim 10, wherein said composition comprises 2,4,5-trimethoxy-N-(tetrazol-5-yl)benzamide.

* * * * *